US00PP24842P2

(12) United States Plant Patent
Wood

(10) Patent No.: US PP24,842 P2
(45) Date of Patent: Sep. 2, 2014

(54) ***HYDRANGEA* PLANT NAMED 'MAKD'**

(50) Latin Name: *Hydrangea serrata*
Varietal Denomination: MAKD

(71) Applicant: Timothy D. Wood, Spring Lake, MI (US)

(72) Inventor: Timothy D. Wood, Spring Lake, MI (US)

(73) Assignee: Spring Meadow Nursery, Inc, Grand Haven, MI (US)

( * ) Notice: Subject to any disclaimer, the term of this patent is extended or adjusted under 35 U.S.C. 154(b) by 92 days.

(21) Appl. No.: 13/573,840

(22) Filed: Oct. 8, 2012

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Annette Para
(74) *Attorney, Agent, or Firm* — C. A. Whealy

(57) ABSTRACT

A new and distinct cultivar of *Hydrangea* plant named 'MAKD', characterized by its low growing and mounding plant habit; strong and sturdy stems; dark green-colored leaves; large lacecap-type inflorescences with double violet-colored sterile flowers; remontant flowering habit; and good garden performance.

3 Drawing Sheets

Botanical designation: *Hydrangea serrata.*
Cultivar denomination: 'MAKD'.

BACKGROUND OF THE INVENTION

The present invention relates to a new and distinct cultivar of *Hydrangea* plant, botanically known as *Hydrangea serrata* and hereinafter referred to by the name 'MAKD'.

The new *Hydrangea* plant is a product of a planned breeding program conducted by the Inventor in Grand Haven, Mich. The objective of the breeding program was to develop new hardy *Hydrangea* plants with strong stems and attractive foliage and flower coloration.

The new *Hydrangea* plant originated from an open-pollination in 2004 of the *Hydrangea serrata* 'Maiko', not patented, as the female, or seed parent and an unknown selection of *Hydrangea serrata* as the male, or pollen, parent. The new *Hydrangea* plant was discovered and selected by the Inventor in 2007 as a single flowering plant within the progeny of the stated open-pollination in a controlled environment in Grand Haven, Mich.

Asexual reproduction of the new cultivar by softwood cuttings in a controlled environment in Grand Haven, Mich. since July, 2007 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'MAKD'. These characteristics in combination distinguish 'MAKD' as a new and distinct *Hydrangea* plant:

1. Low growing and mounding plant habit.
2. Strong and sturdy stems.
3. Dark green-colored leaves.
4. Large lacecap-type inflorescences with double violet-colored sterile flowers.
5. Remontant flowering habit.
6. Good garden performance.

Plants of the new *Hydrangea* differ from plants of the female parent, 'Maiko', in the following characteristics:

1. Plants of the new *Hydrangea* are more mounding than plants of 'Maiko'.
2. Plants of the new *Hydrangea* have double sterile flowers whereas plants of 'Maiko' have single sterile flowers.
3. Plants of the new *Hydrangea* have a remontant flowering habit whereas plants of 'Maiko' do not rebloom.

Plants of the new *Hydrangea* can be compared to plants of *Hydrangea serrata* 'Lynn', disclosed in U.S. Plant Pat. No. 20,019. In side-by-side comparisons, plants of the new *Hydrangea* differ from plants of 'Lynn' in the following characteristics:

1. Plants of the new *Hydrangea* are more mounding than and not as upright as plants of 'Lynn'.
2. Plants of the new *Hydrangea* have double sterile flowers whereas plants of 'Lynn' have single sterile flowers.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'MAKD' grown in a container.

The photograph on the second sheet comprises a side perspective view of a typical flowering plant of 'MAKD' grown in the landscape.

The photograph on the third sheet is a close-up view of a typical flowering plant of 'MAKD'.

DETAILED BOTANICAL DESCRIPTION

Plants used for the aforementioned photographs and the following description were grown during the summer in 5-gallon containers in an outdoor nursery in Grand Haven, Mich. and under cultural practices which closely approximate commercial *Hydrangea* production. Plants of the new *Hydrangea* were grown in acidic soils and were two years old when the photographs and description were taken. In the following description, color references are made to The Royal Horticultural Society Colour Chart, 2001 Edition, except where general terms of ordinary dictionary significance are used.

Botanical description: *Hydrangea serrata* 'MAKD'.

Parentage:

*Female, or seed, parent.*—*Hydrangea serrata* 'Maiko', not patented.

*Male, or pollen, parent*.—Unknown selection of *Hydrangea serrata*, not patented.

Propagation:

*Type cutting*.—By softwood cuttings.

*Time to initiate roots, summer*.—About ten days at temperatures of about 20° C.

*Time to produce a rooted young plant, summer*.—About one month at temperatures of about 20° C.

*Root description*.—Fine to thick, fibrous; white and brown in color.

*Rooting habit*.—Freely branching; dense.

Plant description:

*Plant form and growth habit*.—Perennial deciduous shrub; low growing and mounding plant habit; broad inverted triangle; strong and sturdy lateral branches; freely basal branching habit with about 20 lateral branches developing per plant; vigorous growth habit.

*Plant height*.—About 22 cm.

*Plant diameter or area of spread*.—About 60 cm.

*Lateral branches*.—Length: About 18 cm. Diameter: About 4 mm. Internode length: About 3 cm. Strength: Strong, sturdy. Texture: Smooth, glabrous; longitudinally ridged. Aspect: Erect to about 85° from vertical. Color, developing: Close to 144A. Color, fully developed: Close to 197A.

Foliage description:

*Arrangement*.—Opposite, simple.

*Length*.—About 14 cm.

*Width*.—About 5 cm.

*Shape*.—Lanceolate to ovate.

*Apex*.—Acuminate.

*Base*.—Cuneate.

*Margin*.—Deeply serrate.

*Texture, upper surface*.—Rugose; glabrous.

*Texture, lower surface*.—Rugose; pubescence along the veins.

*Venation pattern*.—Pinnate.

*Color*.—Developing leaves, upper surface: Close to 146B. Developing leaves, lower surface: Close to 146C. Fully expanded leaves, upper surface: Close to 139A; venation, close to 139C. Fully expanded leaves, lower surface: Close to 139B; venation, close to 139C.

*Petioles*.—Length: About 2.2 cm. Diameter: About 3 mm. Texture, upper and lower surfaces: Smooth, glabrous. Color, upper surface: Close to 139B. Color, lower surface: Close to 139C.

Flower description:

*Flower type and habit*.—Double sterile and fertile flowers arranged on large terminal and axillary lacecap-type cymes; inflorescences upright and individual flowers face upright to outwardly.

*Fragrance, fertile flowers*.—Slightly fragrant, pleasant.

*Fragrance, sterile flowers*.—None detected.

*Natural flowering season*.—Flowering remontant from June to August in Grand Haven, Mich.

*Flower longevity, fertile flowers*.—Flowers last about four weeks on the plant; flowers not persistent.

*Flower longevity, sterile flowers*.—Flowers last about three months on the plant; flowers persistent.

*Quantity of flowers*.—Freely flowering; about 195 fertile flowers and about eight sterile flowers develop per inflorescence.

*Inflorescence height*.—About 14 cm.

*Inflorescence diameter*.—About 20 cm.

*Flower diameter, fertile flowers*.—About 1 cm.

*Flower depth (height), fertile flowers*.—About 1.8 cm.

*Flower diameter, sterile flowers*.—About 4.2 cm.

*Flower depth (height), sterile flowers*.—About 2 cm.

*Flower buds, fertile and sterile flowers*.—Length: About 4 mm. Diameter: About 4 mm. Shape: Broadly obovate. Color: Close to 146C.

*Petals, fertile flowers only*.—Arrangement: About 16 arranged in about three whorls. Length: About 2 mm. Width: About 1 mm. Shape: Lanceolate. Apex: Acute. Base: Attenuate. Margin: Entire. Texture, upper and lower surfaces: Smooth, glabrous. Color: When opening and fully opened, upper surface: Close to 92B. When opening and fully opened, lower surface: Close to 92B.

*Sepals, fertile flowers*.—Quantity per flower: Ten in arranged in about two whorls. Length: About 0.5 mm. Width: About 0.5 mm. Apex: Acute. Margin: Entire. Texture, upper and lower surfaces: Smooth, glabrous. Color, upper and lower surfaces: Close to 155B.

*Sepals, sterile flowers*.—Quantity per flower: About twelve arranged in about three whorls. Length: About 2.2 cm. Width: About 1.8 cm. Shape: Broadly ovate. Apex: Retuse or obtuse. Base: Obtuse. Margin: Entire or crenate. Texture, upper and lower surfaces: Smooth, glabrous. Color: When opening and fully opened, upper surface: Close to 92A to 92B. When opening and fully opened, lower surface: Close to 92A to 92B.

*Peduncles, fertile and sterile flowers*.—Length: About 12 cm. Diameter: About 5 mm. Strength: Strong. Aspect: Erect to about 20° from stem axis. Texture: Smooth, glabrous. Color: Close to 144A.

*Pedicels, fertile flowers*.—Length: About 4 mm. Diameter: About 1.5 mm. Strength: Strong. Aspect: Erect to about 45° from stem axis. Texture: Smooth, glabrous. Color: Close to 66D.

*Pedicels, sterile flowers*.—Length: About 3 cm. Diameter: About 2 mm. Strength: Strong. Aspect: About 45° from stem axis. Texture: Smooth, glabrous. Color: Close to 66D.

*Reproductive organs, fertile flowers only*.—Stamens: Quantity per flower: About 20. Anther shape: Rounded. Anther length: Less than 1 mm. Anther color: Close to 66C. Pollen amount: Moderate. Pollen color: Close to 66C. Pistils: Pistil quantity per flower: About five to six. Pistil length: About 1.5 mm. Stigma shape: Oblong. Stigma color: Close to 66D. Style length: About 1.4 mm. Style color: Close to 66D. Ovary color: Close to 66D.

*Seeds*.—Quantity per inflorescence: Numerous. Size: Dust-like, less than 0.1 mm by less than 0.1 mm. Color: Brown.

Disease & pest resistance: Plants of the new *Hydrangea* have been observed to be resistant to Downey Mildew. Plants of the new *Hydrangea* have not been observed to be resistant to pests or other pathogens common to *Hydrangea* plants.

Garden performance: Plants of the new *Hydrangea* have been observed to have good garden performance and to tolerate wind, rain and temperatures ranging from about −25° C. to about 37° C.

It is claimed:

1. A new and distinct *Hydrangea* plant named 'MAKD' as illustrated and described.

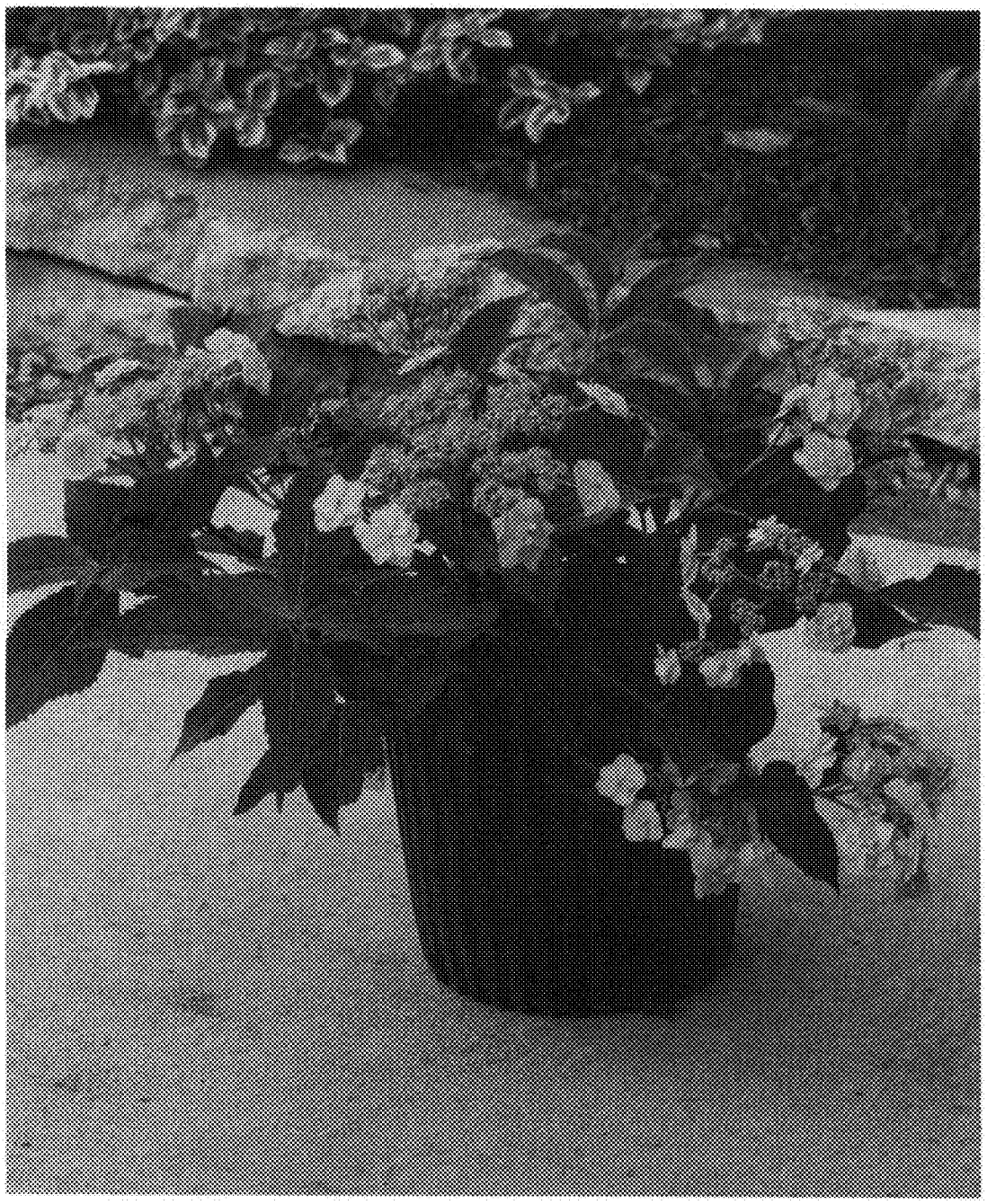

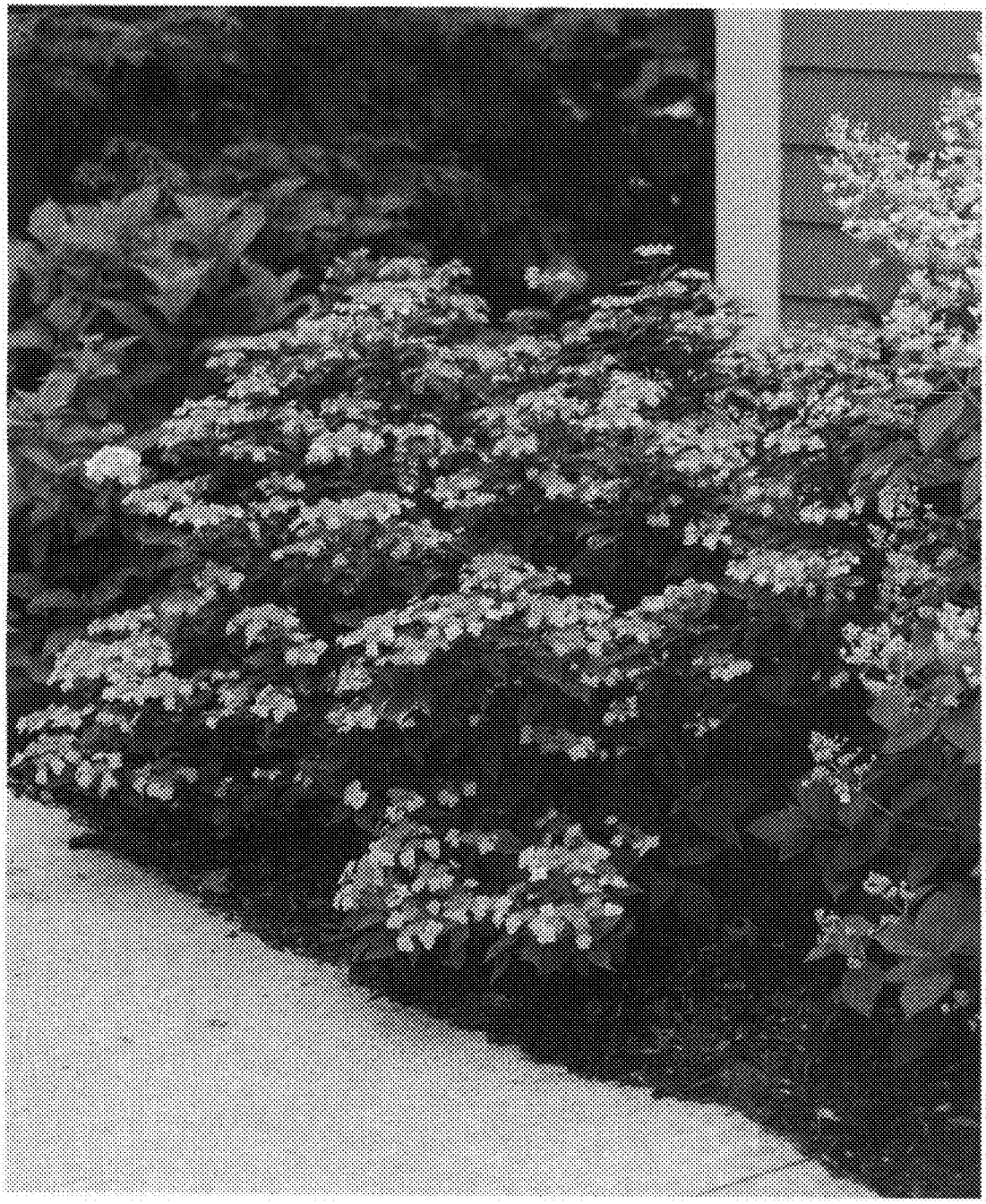

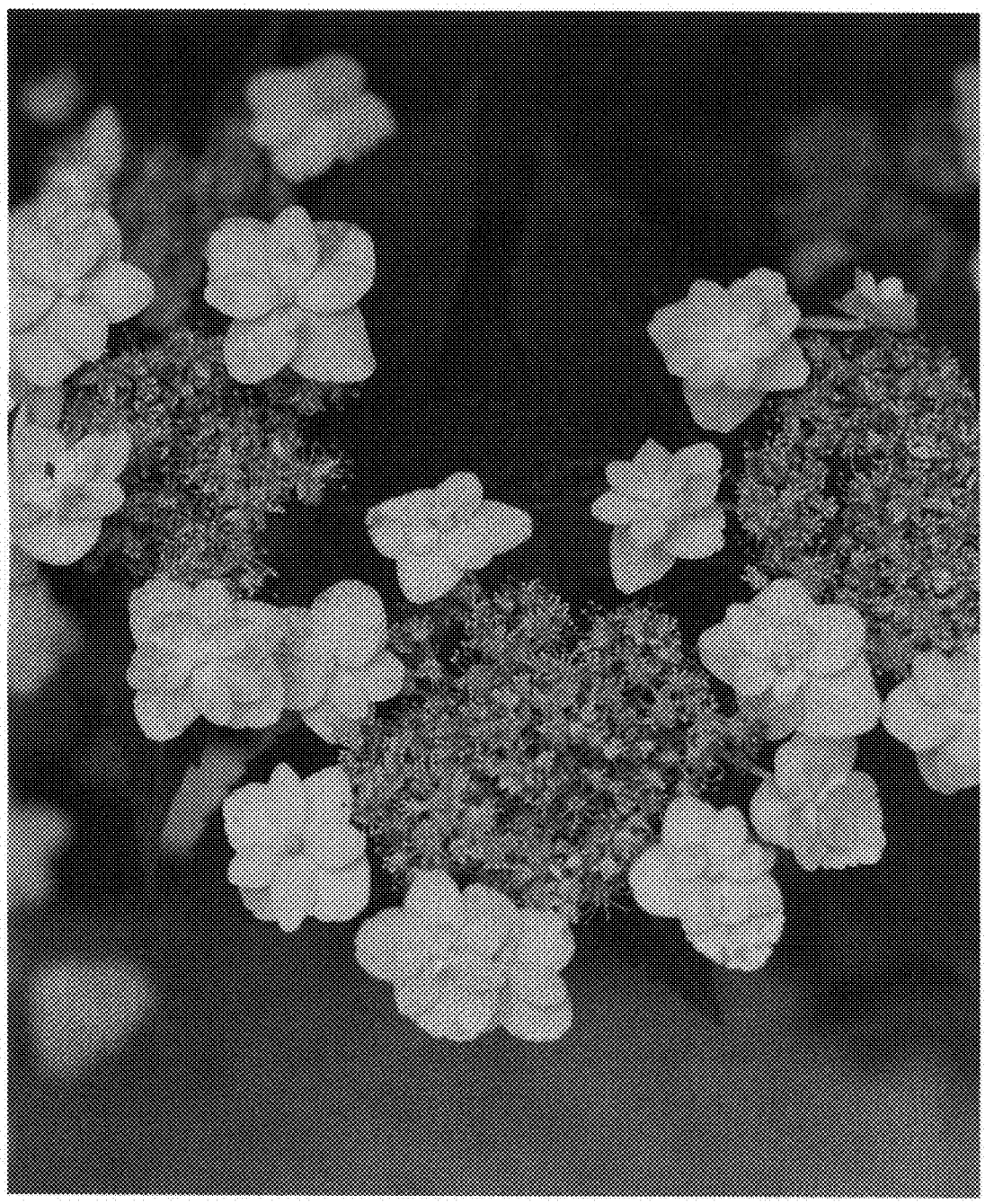

* * * * *